(12) United States Patent
Martens et al.

(10) Patent No.: US 8,770,219 B2
(45) Date of Patent: Jul. 8, 2014

(54) DEVICE AND METHOD FOR REGULATING THE GAS SUPPLY OR THE GAS TRANSPORT IN A GAS STORAGE SYSTEM

(75) Inventors: Christoph Martens, Rockstedt (DE); Jan C. F. Behrens, Seedorf (DE)

(73) Assignee: MT-ENERGIE GmbH, Zeven (DE)

( * ) Notice: Subject to any disclaimer, the term of this patent is extended or adjusted under 35 U.S.C. 154(b) by 364 days.

(21) Appl. No.: 13/129,275

(22) PCT Filed: Nov. 13, 2009

(86) PCT No.: PCT/EP2009/008088
§ 371 (c)(1),
(2), (4) Date: Aug. 5, 2011

(87) PCT Pub. No.: WO2010/054827
PCT Pub. Date: May 20, 2010

(65) Prior Publication Data
US 2011/0303299 A1    Dec. 15, 2011

(30) Foreign Application Priority Data
Nov. 15, 2008  (DE) .................. 10 2008 057 586

(51) Int. Cl.
*F04F 1/06*    (2006.01)
(52) U.S. Cl.
USPC .......................................... 137/208; 137/209
(58) Field of Classification Search
USPC ......... 137/592, 583, 584, 572, 576, 208, 209, 137/206, 571; 210/137; 62/50.7; 220/720, 220/560.08
See application file for complete search history.

(56) References Cited

U.S. PATENT DOCUMENTS

| | | | |
|---|---|---|---|
| 3,433,147 A * | 3/1969 | Pedersen | 99/455 |
| 4,437,987 A | 3/1984 | Thornton et al. | |
| 4,902,304 A * | 2/1990 | Hallen | 48/174 |
| 5,479,966 A * | 1/1996 | Tison et al. | 141/4 |
| 6,231,009 B1 * | 5/2001 | Kong | 244/135 R |
| 6,810,925 B2 * | 11/2004 | Graham et al. | 141/98 |

FOREIGN PATENT DOCUMENTS

| | | |
|---|---|---|
| AT | 388 158 B | 5/1989 |
| DE | 689 22 151 T2 | 9/1995 |
| DE | 20 2004 020 394 U1 | 8/2005 |
| EP | 0 333 698 A2 | 9/1989 |
| EP | 0 350 455 A2 | 1/1990 |
| EP | 1 447 613 A2 | 8/2004 |
| WO | 2005/075951 A1 | 8/2005 |

* cited by examiner

*Primary Examiner* — Craig Schneider
*Assistant Examiner* — Angelisa Hicks
(74) *Attorney, Agent, or Firm* — Vidas, Arrett & Steinkraus, P.A.

(57) ABSTRACT

A device for regulating the gas supply in a gas storage system of a biogas system, wherein the gas storage system has gas stores connected in series in a cascade-like manner with an intermediate chamber between a gas store membrane and a protective cover. The device comprises gas supply mechanisms, intermediate chamber pressure measuring mechanisms and at least one regulating mechanism, each gas store is assigned at least one gas supply mechanism, each gas store is assigned at least one intermediate chamber pressure measuring mechanism with which the gas pressure in the intermediate chamber of the respective gas store can be measured, and the measured values of the intermediate chamber pressure measuring mechanisms are transmitted to at least one regulating mechanism, and the regulating mechanism is designed to regulate the gas pressure in the intermediate chambers of the gas stores by controlling the gas supply mechanisms assigned to gas stores.

20 Claims, 2 Drawing Sheets

DEVICE AND METHOD FOR REGULATING THE GAS SUPPLY OR THE GAS TRANSPORT IN A GAS STORAGE SYSTEM

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention relates to a device and a method for regulating the gas supply or the gas transport in a gas storage system of a biogas system, where the gas storage system has at least two gas stores connected in series in a cascade-like manner.

Known biogas systems often have several gas stores in the form of covered fermenters that are connected in series in a cascade-like manner in a gas network system. The tanks are frequently covered with an inflatable foil cover that forms a double membrane cover. A gas store membrane, for example a gas store foil, is installed over the top opening and edges of the fermenter. A protective cover, for example, a weather protection foil, is also installed over the gas store foil. The gas store foil and the weather protection foil are connected to the top of the fermenter wall in a gas-tight, force-fit connection. It is known to introduce air into the intermediate chamber formed between the gas store foil and the weather protection foil, by means of a supporting air blower. In this manner, the shape stability of the weather protection foil is guaranteed, and an undesired impact on the shape stability from snow or rain water, for instance, is avoided. The introduced air can escape again via at least one pressure regulating ventilation opening, a cross-flow flap for example, also provided in the intermediate chamber. The flap is loaded with weights that regulate the back pressure of the outlet, and thus, create the system pressure for the respective gas store. The gas store foil can largely freely move up and down underneath the dimensionally stable weather protection foil, and thereby provide the gas store volume in the tank of the biogas system.

The gas of the biogas system, produced in the fermentation tanks, fermenters for example, is typically cleaned using a biological desulfurization. Thiobacteria, which are naturally present, are responsible for the biological breakdown of hydrogen sulfide ($H_2S$) in the gas phase. Thiobacteria transform $H_2S$ into sulfuric acid and elementary sulfur in an aerobic process. The reaction equations are represented in the following:

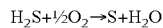  1)

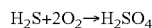  2)

Sufficient oxygen must be present in the gas phase for desulfurization. For this reason, air or oxygen is introduced in defined quantities into the fermenter above the respective fermentation substance. Furthermore, a sufficiently large colonization surface must be present for the microorganisms (e.g., netting). The quality of the gas treatment depends on, among other things, the dwell time of the gas in the biogas system. In unheated fermentation product stores in the biogas system, the gas can cool off during passage through the tanks disposed in a cascade-like manner, and can thus release a portion of the moisture contained in the gas.

It is known to connect multiple gas stores in series, where gas pipelines through which the gas is transported run between the gas stores. Because gas transport can occur particularly without a gas condenser, the pressure must decrease from one store to the next one. There are further pressure losses in the gas pipelines. A starting pressure prevails in a first gas store that must not exceed a predetermined maximum value because of the structural conditions, particularly the static design of the foil covering. A minimum pressure should still prevail in the final gas store of system so that the gas can be removed from this gas store without any problems.

Therefore, it is necessary to regulate the pressure in the individual gas stores. The fermentation pressure prevailing above the fermentation substance can in the process be influenced by controlling the pressure prevailing in the intermediate chamber between the gas store foil and the weather protection foil, where the gas store foil acts as a membrane. With a cascaded connection of the gas store tanks, the tank pressures are typically regulated using the weights acting on the respective ventilation flaps. With this, the supporting air blowers are operated continuously.

It is attempted in practice to produce a balance in the system during commissioning of the system, so that the gas flows through the series of gas stores. However, if the state and the influences on the system change after the start-up phase (e.g., due to changed gas production quantities or seasonal climate change), the system cannot react automatically to the changes. This can lead to disruptions of the gas flow. In order to adapt the sensitive tuning of the gas pressures, it is therefore often necessary that an on-site operator changes the weight applied to the ventilation flaps. This requires significant effort. Furthermore, a flexible reaction to changed operating conditions is hardly possible without considerable intervention by on-site personnel. This is particularly true if the gas stores are to be completely emptied within a short time period for maintenance or repair purposes.

In addition there is the fact that the weights do not always permit a sufficiently fine pressure setting adjustment. Particularly with larger cascade connections, for example of more than four tanks, occasionally extremely small differential pressures must be adjusted between the tanks due to the predetermined maximum staring pressure in the first tank and the similarly predetermined minimum pressure in the last tank. However, in practice it is not always possible to implement such small pressure differences due to the relatively coarse adjustment possibilities using the weights.

BRIEF SUMMARY OF THE INVENTION

Starting from the described prior art as a background, the object of the present invention is therefore to provide a device and a method of the initially named type, with which gas storage management is possible in a simple, flexible and precise manner.

The objective of the invention is solved for a device of the initially named type according to a first aspect in that the gas stores in each case have an intermediate chamber between a gas storage membrane and a protective covering, and that the device comprises gas supply mechanisms, intermediate chamber pressure measuring mechanisms and at least one regulating mechanism, wherein each gas store is assigned at least one gas supply mechanism with which gas can be supplied to the intermediate chamber of the respective gas store, wherein each gas store is assigned at least one intermediate chamber pressure measuring mechanism with which the gas pressure in the intermediate chamber of the respective gas store can be measured, wherein the measured values of the intermediate chamber pressure measuring mechanisms are transmitted to the at least one regulating mechanism, and wherein the at least one regulating mechanism is designed to regulate the gas pressure in the intermediate chambers of the gas stores based on the valued measured by the intermediate chamber pressure measuring mechanisms by controlling the gas supply mechanisms assigned to each of the gas stores.

The objective of the invention is solved additionally according to a first aspect by a method of the initially named type comprising the steps: supplying gas to each intermediate chamber of the gas store, measuring the gas pressure in each case in the intermediate chamber, and on the basis of the measured gas pressure in the intermediate chambers in each case, regulating the gas pressure in the intermediate chamber by controlling the gas supply into intermediate chamber.

According to a second aspect, the objective of the invention is solved for a device of the initially named type wherein the device comprises at least one regulating mechanism, wherein store chambers of the gas store for gas, for example for biogas generated in the gas store, are each connected together by at least one gas overflow line, wherein at least one gas condenser is disposed in the at least one gas overflow line, and wherein the at least one regulating mechanism is designed for regulating the performance of the at least one gas condenser so that gas is transported between the store chambers of the gas store via the at least one gas overflow line.

In addition, the objective of the invention is solved for a method of the initially named type according to the second aspect in that store chambers of the gas stores for gas, for biogas generated in the gas store, for example, are each connected together by at least one gas overflow line, wherein at least one gas condenser is disposed in the at least one gas overflow line, and wherein the performance of the at least one gas condenser is regulated so that gas is transported between the store chambers of the gas stores via the at least one gas overflow line.

Naturally, the gas stores according to the second aspect of the invention can also have an intermediate chamber between a gas store membrane and a protective covering. According to the first aspect of the invention, a regulation of the gas pressure occurs in the intermediate chamber between the gas store membrane and the protective covering of each gas store. According to the second aspect of the invention, a control of the performance of the at least one gas condenser takes place. The gas store membrane can be a gas store foil, and the protective covering can be a protective foil, particularly a weather protection foil. Naturally, a fixed protective covering is also conceivable. The gas stores can be covered fermenters of the biogas system, in which correspondingly a fermentation substance can be held. However, it can also be a gas store in which there is no fermentation substance. The controlled process variable according to the first aspect of the invention is the gas pressure measured in the intermediate chamber. The correcting variable is the gas supply via the respective gas supply mechanism. The regulation or regulating mechanism can be designed according to the first and the second aspect of the invention for the purpose of regulating the gas pressure in the respective intermediate chamber or the performance of the at least one gas condenser so that the gas pressure and/or the performance do not exceed a predetermined maximum value and/or do not fall below a predetermined minimum value, thus, remaining in a predetermined interval. The gas pressure or the performance of the at least one gas condenser can also be regulated towards a specific predetermined target value. The maximum and minimum values or target values can be predefined individually for each gas store. In particular according to the first aspect, air, for example, can be supplied as a gas into the intermediate chamber for pressure generation. The gas supply mechanism can, in a known manner, be supporting air blowers. For transporting the gas, particularly according to the second aspect, known gas condensers can be used.

In each case, a fermentation substance is located in the gas stores. The invention makes possible in a simple manner an exact adjustment of the gas pressure in the respective intermediate chamber or the performance of the at least one gas condenser, and with it, also of the gas pressure above the fermentation substance contained, where applicable, in the respective gas store. In the process, the regulation can be automatic. In contrast to the prior art, particularly with the first aspect of the invention, it is no longer necessary to continuously operate the gas supply mechanism. This results in energy savings. Furthermore, by regulating the gas pressure in the intermediate chamber and with it, also in the actual gas store chamber, an unloading of the optionally provided inflatable foil cover can be attained, even in high pressure situations, by switching off the blowers. The system stabilizes itself automatically by means of the control function. Because according to the invention, the pressure in the gas stores or the performance of the gas condenser can be regulated with a high degree of accuracy, even small differential pressures can be realized between gas stores connected in series in a cascade-like manner, or gas transport can be guaranteed between the tanks due to a pressure increase. Thereby, in contrast to the prior art, a larger number of gas stores can be connected. This way, in turn, the gas quality increases. For maintenance procedures also, in which a rapid emptying or movement of gas in the gas stores is to occur, for example, the invention is advantageous. In particular, the gas movement or emptying can be accelerated by exerting targeted influence on the gas store pressure or on the performance of the gas condenser. In summary, according to both aspects of the invention, an effective gas store and load management of the biogas system is possible in a simple and flexible manner.

The inventive device and the inventive method can naturally serve for regulating the gas supply into intermediate chambers between gas store membranes and protective coverings, or for regulating the performance of gas condensers of more than two gas stores of a biogas system. In particular, the biogas system can then have 3, 4 or more than 4 gas stores, for example. Using the regulating mechanism then in the inventive manner, the intermediate chamber pressures as well as the fermenter pressures or the gas condenser performances can, in turn, be individually regulated for the individual gas stores. The gas supply mechanisms of the individual gas stores can each have their own supporting air blower. However, it is also conceivable that a few components of the gas supply mechanisms are common to several gas supply mechanisms. In the most simple case, the gas supply mechanisms each have only an individual gas supply line into the respective intermediate chamber. A combination of the first and second aspects of the invention is also possible.

According to one embodiment, the regulating mechanism can be designed to regulate the gas pressure in a respective intermediate chamber of a gas store on the basis of a preset target value for the gas pressure in the intermediate chamber of this gas store, and on the basis of target value for the gas pressure in the intermediate chamber of at least one other gas store. In this embodiment, measured values of intermediate chamber pressure measuring mechanism assigned to the respective gas store, and measured values of intermediate chamber pressure measuring mechanisms assigned to the other gas stores, in particular, all intermediate chamber pressure measuring mechanisms, can be considered for the pressure regulation of the respective gas store. In this way, in a cascade arrangement of several gas stores, particularly several fermenters, it is possible to coordinate the pressure in the individual gas stores to each other. Thus, a pressure difference between gas stores disposed in a gas network can be predetermined and adjusted by means of the regulation. Thus, the gas transport between the gas stores can be optimized.

According to a further embodiment, it can be provided that the gas stores are each assigned store chamber pressure measuring mechanisms with which the gas pressure in the store chambers can be measured, and that at least one regulating mechanism is designed to regulate the performance of at least one gas condenser on the basis of the measured values of the store chamber pressure measuring mechanisms at least of the gas stores, which are connected by the gas overflow line provided with the at least one gas condenser. With this embodiment, the at least one gas condenser can be regulated by means of the gas pressure of the tanks on the suction side as well as the pressure side of the gas condensers. Gas pressure sensors that continuously output the actual gas pressure can be used for the store chamber pressure measuring mechanisms so that the gas condenser can be regulated using an evaluation unit. However, simple pressure monitors, for example, can also be used that upon exceeding or falling below set threshold values, switch a switching output by means of which the gas condenser(s) are regulated, with or without further control.

According to a further embodiment, fill level measuring mechanisms can be assigned to each of the gas stores with which a gas fill level in the store chambers of the gas stores can be measured, wherein the at least one regulating mechanism is designed for the purpose of regulating the performance of the at least one gas condenser based on the measured values of the fill level measuring mechanisms of at least the gas stores, which are connected through the gas overflow line provided with the at least one gas condenser. Thus, the at least one gas condenser is regulated via the fill level of the gas store at a suction side as well as the pressure side of the gas condenser.

The at least one gas condenser can further be dimensioned so that even at maximum performance of the gas condenser, the occurrence of an impermissible overpressure or underpressure is avoided in one of the gas stores. Thus, the at least one gas condenser, due to "under-dimensioning", is not in a position to do damage or can possibly incur an emergency switch off due to overpressure or under pressure switch contacts.

Furthermore, a regulating mechanism can be assigned to each gas condenser. The individual roof pressures or the individual gas condenser can therefore be regulated using control units that are independent of each other.

According to a further embodiment, the device can further comprise store chamber pressure measuring mechanisms, wherein each gas store is assigned at least one store chamber pressure measuring mechanism with which the gas pressure in the gas store chamber can be measured beneath the gas store membrane, and wherein the measured values of the store pressure measuring mechanisms are also transmitted to the regulating mechanism and are considered during the regulation of the gas pressure in the intermediate chambers. By an additional measurement of the gas pressure in the store chamber, more information is acquired regarding the overall state of the system, particularly with respect to how the pressure in the intermediate chambers and the store chambers differ in the case of an expansion of the gas store foil, for example. The system can be adjusted even more effectively in that the additional pressure measurement is considered with the regulation. At the same time, a fermentation substance can be contained in the gas stores. In this case, the gas pressure in the store chamber above the fermentation substance is measured by the store chamber pressure measuring mechanisms. The fermentation pressure in the gas store, in this context, indicates the pressure in the store chamber of the gas store (directly) above the respective fermentation substance. Measured values of the store chamber pressure measuring mechanism assigned to the respective gas store and measured values of store chamber pressure measuring mechanisms assigned to other gas stores, and particularly all store chamber pressure measuring mechanisms, can in turn be considered for the regulation of the pressure in one gas store.

The regulating mechanism can further be designed for controlling the gas supply mechanisms so that the gas pressure in the intermediate chambers does not exceed a predetermined maximum value. The regulation is therefore based on the respectively higher measured pressure value. Thus, it can be prevented that an impermissibly high pressure can develop in the intermediate chambers. Because of the pressures in the intermediate chamber and the store chamber influence each other, as explained initially, by regulating the gas supply into the intermediate chamber the pressure in the store chamber can also be influenced.

If the store chamber beneath the gas store membrane is completely filled however, the gas store membrane stretches and the pressure in the store chamber increases above the predetermined maximum value of the regulating mechanism, so that the gas supply mechanism remains switched off. In order to avoid that the pressure in the intermediate chamber decreases so far that the protective covering, for example the weather protector foil, loses its shape stability, a minimum pressure regulator can be provided. This means that the gas supply mechanisms are controlled by the regulating mechanism so that the gas pressure in the intermediate chambers of the gas stores does not fall below a predetermined minimal value.

According to a further embodiment in this regard, the regulating mechanism can be designed in a way to regulate the gas pressure in the intermediate chambers within the interval predetermined by the maximum value and the minimum value so that the gas pressure in the gas store chambers comes as close as possible to a target value. In this embodiment, a target value that permits an optimal gas store and load management, particularly an optimized gas transport between the gas stores, is predetermined for the pressure in the store chamber beneath the gas store membrane, for example above the fermentation substance. Depending on the prevailing operating and pressure conditions, it is possible, by regulating the intermediate chamber pressure within the interval permissible for the intermediate chamber pressure, to select a pressure so that the store pressure in the gas store chamber comes as close as possible, or attains, the predetermined target value. The limits for this indirect pressure regulation in the store chamber represent the permissible interval limits for the intermediate chamber pressure.

The maximum, minimum and/or target values for the pressures can according to the invention each be predetermined individually for each gas store.

According to a further embodiment, an on-off regulation can be preformed. Thus, the gas supply mechanism can be controlled, in particular, solely by the on or off switching. This results in a particularly simple regulation, in that upon falling below a predetermined minimal value for the pressure, the gas supply is switched on, and upon exceeding a predetermined maximum value for the pressure, the gas supply is switched off. The system conditions prevailing in biogas systems can often be sufficiently precisely represented by such an on-off regulation. Naturally however another control is also possible, for example a continuous control using a suitable control mechanism, which comprises frequency converters, for example.

The intermediate chambers of the gas stores, according to a further embodiment, can each be ventilated using it least one pressure regulated ventilation opening. Such a ventilation opening can be, for example a weighted ventilation opening, for example a ventilation flap, in particular a cross-flow flap. The aeration and ventilation behavior of the system, and thus, the switching frequencies of the regulation, are predetermined by a suitable weighting of the opening. By intelligent tuning of the pressure regulation, of a weighting, for example, it is possible to determine a suitable operating range for each gas store that can be covered by the regulation. Thus, also in the case of changes of the system conditions after commissioning, a flexible fine tuning is possible using the regulation, without requiring a change of the weighting.

According to a further advantageous embodiment, the regulating mechanism can be controlled from a site located remotely from the biogas system. Thus, remote operation of the regulation is possible, and with it, a remote control of the regulation parameters in the respective predetermined operating range is possible. Similarly then, the respectively prevailing conditions of the system can be monitored at a site that is remote from the system.

According to the invention, the gas in the biogas system can be supplied from one gas store to the other, over a longer time period in a controlled manner. Overall, better gas quality is attained. The gas store management made possible by the invention is flexible, simple and precise. Remote access permits convenient monitoring and regulation of the system.

The invention solves the objective also by a biogas system having an inventive device. The inventive device can be suitable for performing the inventive method.

BRIEF DESCRIPTION OF THE SEVERAL VIEWS OF THE DRAWINGS

An exemplary embodiment of the invention is explained in the following in more detail using a drawing. The drawing shows schematically in.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

Figure 1:
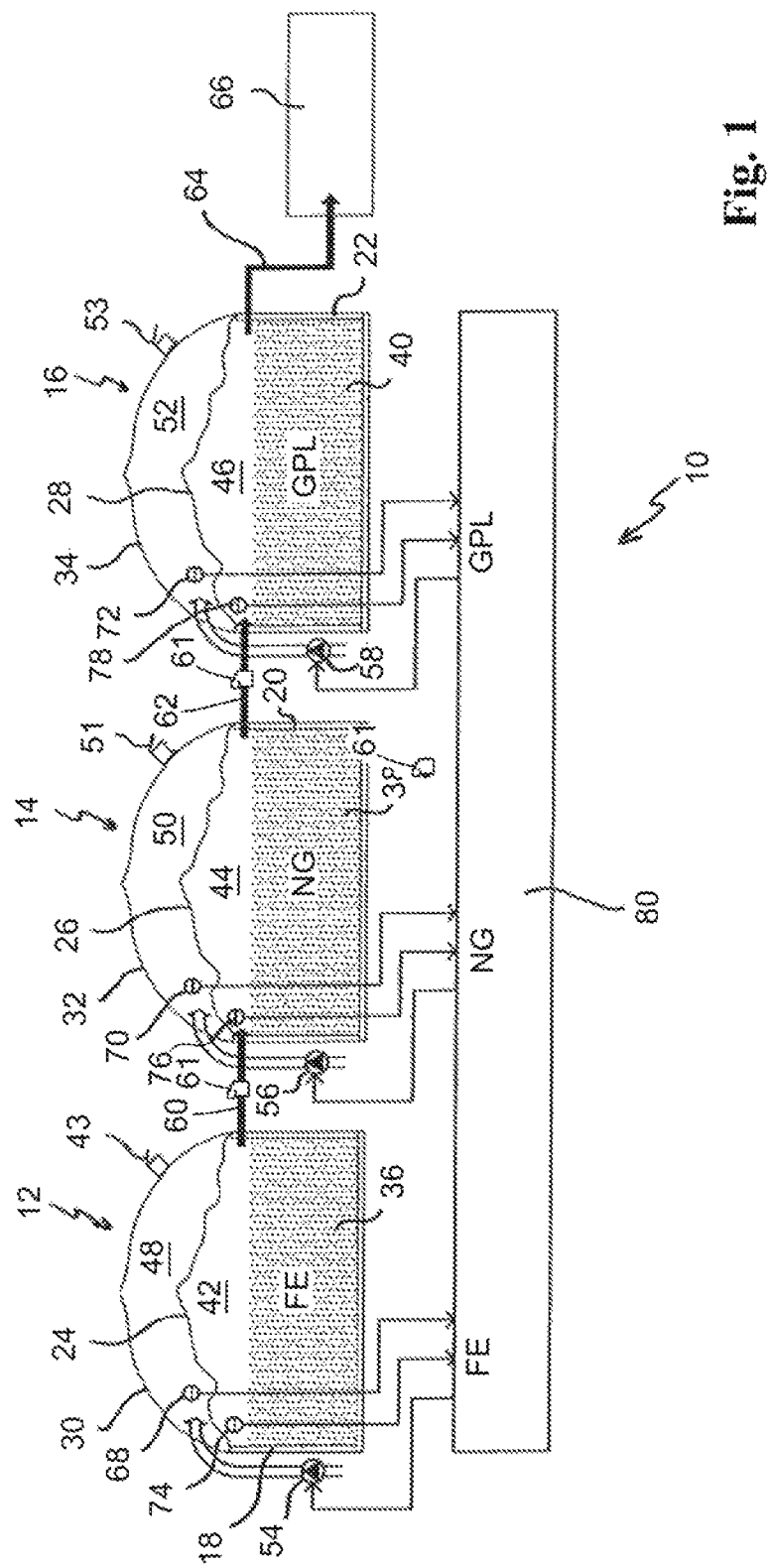
FIG. 1 an inventive device in a partial sectional view,
FIG. 2 a graph for illustrating the response behavior with different weightings of a ventilation flap, and
FIG. 3 a further graph for illustrating the response behavior depending on the weighting.

In the figures, the same reference numbers refer to the same objects unless indicated otherwise. FIG. 1 shows an inventive device 10 for regulating the gas supply in an intermediate chamber between a gas store membrane and a protective cover of at least two gas stores, of three present fermenters of a biogas system. The biogas system has three gas stores 12, 14, 16 present in the form of three tanks 12, 14, 16 that are connected in series in a cascade-like manner. Each of the tanks 12, 14, 16 has a cylindrical shape. A gas store membrane, present as a gas store foil 24, 26, 28 is attached in a gas-tight and force-fit manner to the top of the respective tank wall 18, 20, 22. A protective cover, present as a weather protection foil 30, 32, 34 is fastened, also gas-tight and force-fit, to head of the wall and above the gas store foil 24, 26, 28. The foils form an inflatable foil cover as a double membrane. For generating biogas, a fermentation substance 36, 38, 40 is filled into the tanks 12, 14, 16. The biogas developing above the fermentation substance 36, 38, 40 fills the respective store chamber 42, 44, 46 above the fermentation substance 36, 38, 40 and below the gas store foil 24, 26, 28. Gas, in the represented example, air, is blown into the respective intermediate chambers 48, 50, 52 between the gas store foils 24, 26, 28 and the weather protection foils 30, 32, 34. For this purpose, a gas supply mechanism 54, 56, 58, present in each case as a supporting air blower 54, 56, 58, is assigned to each tank 12, 14, 16. Furthermore, at least one ventilation flap 49, 51, 53, in the example shown in each case a cross-flow flap 49, 51, 53, is assigned to each intermediate chamber 48, 50, 52. The ventilation flaps 49, 51, 53 are loaded with weights that regulate the back pressure of the blower outlet. The weather protection foils 30, 32, 34 are held in stable shape in this manner. The gas store foils 24, 26, 28, in contrast, can move up and down depending on the fill level in the store chambers 42, 44, 46. The individual tanks 12, 14, 16 are connected together via gas overflow lines 60, 62. Gas developing in the store chamber 42 of the first tank 12 can arrive in the store chamber 44 of the second tank 14 via the line 60. Gas from the store chamber 44 of the second tank 14 can, in turn, arrive in the store chamber 46 of the third tank 16 via the line 62. The first tank is a so-called fermenter (FE), the second tank is a so-called post-fermenter (NG), and the third tank is a so-called fermentation storage tank (GPL). The gas from the third tank 16, travels via line 64 for further utilization, for example, with a consumer 66. This design of a biogas system is known.

Furthermore, in each intermediate chamber 48, 50, 52, an intermediate chamber pressure measuring mechanism 68, 70, 72 is disposed that measures the gas pressure in the respective intermediate chamber 48, 50, 52. In addition, in each of the store chambers 42, 44, 46, a store chamber measuring mechanism 74, 76, 78, a fermenter pressure measuring mechanism 74, 76, 78 in the example shown, is disposed that measures the gas pressure in the respective store chamber 42, 44, 46 below the gas store foils 24, 26, 28 and above the respective fermentation substance 36, 38, 40. The measured values of the pressure measuring mechanisms 68, 70, 72 and 74, 76, 78 are supplied to a regulating mechanism 80. The regulating mechanism 80 regulates the gas pressure individually in the intermediate chambers 48, 50, 52 of the tanks 12, 14, 16, as well as in the store chambers 42, 44, 46, on the basis of the respective measured values of the measuring mechanisms 68, 70, 72 and 74, 76, 78. For this purpose, the regulating mechanism 80 individually controls gas supply mechanisms 54, 56, 58, respectively assigned to the tanks 12, 14, 16, in a suitable manner. In the example shown, the regulating mechanism 80 controls the blowers 54, 56, 58 respectively so that in each tank 12, 14, 16 the intermediate chamber pressure as well as the store chamber pressure remain below a predetermined maximum value. Additionally, the regulating mechanism 80 controls the blowers 54, 56, 58 so that the intermediate chamber pressure does not fall below a minimum value so the shape stability of the weather protection foil is guaranteed at all times. In the example shown, the regulating mechanism 80 is disposed on-site of the biogas system, and can be controlled, for example, by a suitable remote control mechanism that is remote from the system.

Alternatively or in addition to the intermediate chamber pressure control described above, gas can also be transported via a performance control of gas condensers. For this purpose, a gas condenser 61, can be disposed in the gas overflow lines 60, 62 between the gas stores 12, 14, 16. The performance of the gas condensers 61 can be controlled by the regulating mechanism 80, in each case on the basis of the measured gas pressure in the gas store chambers of those respective gas stores, which are connected by the respective gas overflow line 60, 62 provided with the gas condenser. Alternatively or in addition, the gas condensers 61 can be regulated also in each case on the basis of the measured fill levels at least in the respective gas stores that are connected by the respective gas overflow line (60, 62) provided with the gas condenser 61.

Figure 2:
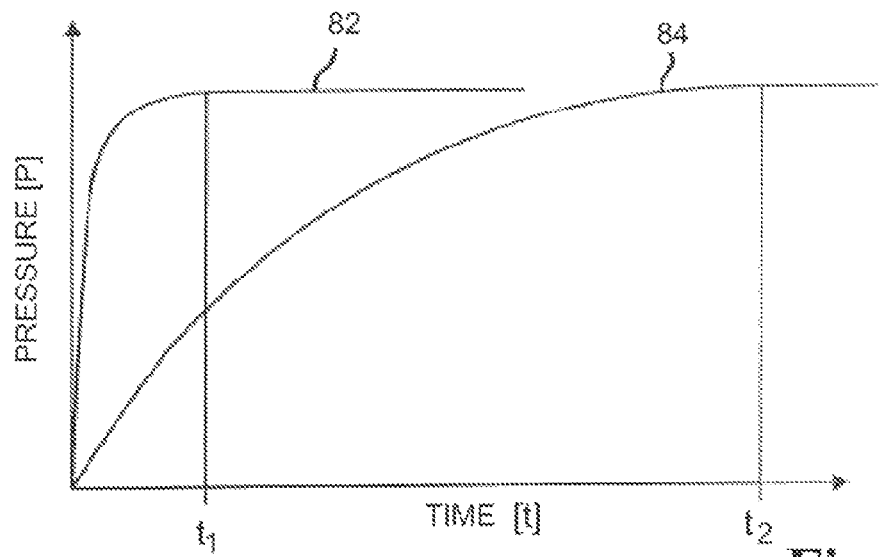

FIG. 2 shows a graph for illustrating the effects of different weightings of the ventilation flaps 49, 51, 53 of the intermediate chambers 48, 50, 52 of the tanks 12, 14, 16 of the biogas system. The pressure P in the respective intermediate chamber 48, 50, 52 is plotted against the time t with aeration of the intermediate chambers 48, 50, 52. The curve 82 shows by way of example an increasing pressure course with constant performance of the support air blowers 54, 56, 58 and a high weighting of the ventilation flaps 49, 51, 53. The pressure P increases rapidly in a short time, and attains saturation at time $t_1$. The curve 84 in FIG. 2 shows the pressure course with the same performance of the support air blowers 54, 56, 58 as with the curve 82, however, with a lower weighting of the ventilation flaps 49, 51, 53. The pressure P in the intermediate chamber increases considerably more slowly, and attains the saturation only at a significantly later time $t_2$.

Figure 3:
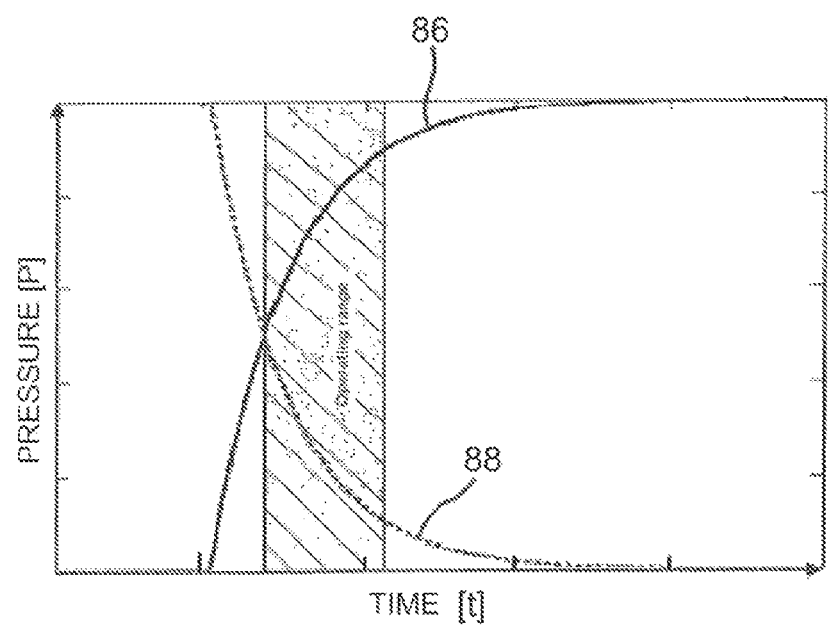

FIG. 3 show a further graph for illustrating the response with aeration and ventilation of the biogas system with constant performance of the support air blowers 54, 56, 58. Again, the pressure P in the respective intermediate chamber 48, 50, 52 is plotted against time t. The curve 86 shows the pressure course with aeration of the respective intermediate chambers 48, 50, 52. The curve 88 in FIG. 3 shows the corresponding pressure course with ventilation of the intermediate chamber 48, 50, 52. The hatched region in the graph represents the operating range within which the pressure in the intermediate chambers 48, 50, 52 can be regulated during operation by means of the regulating mechanism.

In the operation of the system, a comprise must be found for the weighting that allows possibly all necessary pressures, within the scope of operation of the system, in the intermediate chambers 48, 50, 52 and in the store chambers 42, 44, 46 to be adjusted by means of the regulating mechanism 80.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A device for regulating the gas supply in a gas storage system of a biogas system, wherein the gas storage system has at least two gas stores connected in series in a cascade-like manner that each have an intermediate chamber between a gas store membrane and a protective covering
the device comprises gas supply mechanisms (54, 56, 58), intermediate chamber pressure measuring mechanisms (68, 70, 72) and at least one regulating mechanism (80), wherein to each gas store (12, 14, 16) at least one gas supply mechanism (54, 56, 58) is assigned with which gas can be supplied to the intermediate chamber (48, 50, 52) of the respective gas store (12, 14, 16),
wherein to each gas store (12, 14, 16) at least one intermediate chamber pressure measuring mechanism (68, 70, 72) is assigned with which the gas pressure in the intermediate chamber (48, 50, 52) of the respective gas store (12, 14, 16) can be measured, wherein the measured values of the intermediate chamber pressure measuring mechanisms (68, 70, 72) are supplied to at least one regulating mechanism (80), and
wherein the at least one regulating mechanism (80) is designed to regulate the gas pressure in the intermediate chambers (48, 50, 52) of the gas stores (12, 14, 16), on the basis of the measured values of the intermediate chamber pressure measuring mechanisms (68, 70, 72), by a control of the gas supply mechanisms (54, 56, 58) assigned respectively to the gas stores (12, 14, 16).

2. The device according to claim 1, characterized in that the at least one regulating mechanism is designed to regulate the gas pressure in a respective intermediate chamber (48, 50, 52) of a gas store (12, 14, 16), on the basis of specified target value for the gas pressure in the intermediate chamber of this gas store and a target value for the gas pressure in the intermediate chamber of at least one other gas store.

3. The device according to claim 1, wherein each gas store (12, 14, 16) is assigned a regulating mechanism.

4. The device according to claim 1, wherein the device further comprises store chamber measuring mechanisms (74, 76, 78), wherein each gas store (12, 14, 16) is assigned at least one store chamber measuring mechanism (74, 76, 78), with which the gas pressure in the gas store chamber below the gas store membrane can be measured, and wherein the measure values of the store chamber measuring mechanisms (74, 76, 78) are also transmitted to the regulating mechanism (80) and are considered with the regulation of the gas pressure in the intermediate chambers (48, 50, 52).

5. The device according to claim 1, wherein the regulating mechanism (80) is designed to control the gas supply mechanisms (54, 56, 58) so that the gas pressure in the intermediate chambers (48, 50, 52) does not exceed a specified maximum value.

6. The device according to claim 1 wherein the regulating mechanism (80) is designed to control the gas supply mechanisms (54, 56, 58) so that the gas pressure in the intermediate chambers (48, 50, 52) does not fall below a specified minimum value.

7. The device according to claim 5, wherein the regulating mechanism (80) is designed to regulate the gas pressure in the intermediate chambers (48, 50, 52) within the interval specified by the maximum value and the minimum value, so that the gas pressure in the gas store chamber comes as close as possible to a target value.

8. The device according to claim 1, wherein the regulating mechanism (80) performs an on-off control.

9. The device according to claim 1, characterized in that the intermediate chambers (48, 50, 52) each have at least one pressure regulating ventilation opening (49, 51, 53).

10. The device according to claim 1, wherein the regulating mechanism (80) can be controlled from a location remote from the biogas system.

11. A method for regulating the gas supply in a gas storage system of a biogas system, wherein the gas storage system has at least two gas stores connected in series in a cascade-like manner, each of which has an intermediate chamber between a gas store membrane and a protective cover, comprising the steps:
supplying gas to each of the intermediate chambers (48, 50, 52) of the gas stores (12, 14, 16),
measuring the gas pressure in each of the intermediate chambers (48, 50, 52), and
regulating the gas pressure in the intermediate chambers (48, 50, 52), on the basis of the measured gas pressures in the intermediate chambers (48, 50, 52), by controlling the gas supply into the intermediate chambers (48, 50, 52).

12. The method according to claim 11, characterized in that the gas pressure in a respective store chamber (48, 50, 52) of a gas store is regulated, on the basis of a target value for the gas pressure in the intermediate chamber, and a target value for the gas pressure in the intermediate chamber of at least another gas store.

13. The method according to claim 11, wherein each gas store (12, 14, 16) is assigned a regulating mechanism.

14. The method according to claim 11, wherein further the gas pressure (12, 14, 16) in the gas store chamber below the gas store membrane is measured, wherein the gas pressure measured in the gas store chamber is considered during regulation of the gas pressure in the intermediate chambers (48, 50, 52).

15. The method according to claim 14, characterized in that the gas supply is controlled so that the gas pressure in the intermediate chambers (48, 50, 52) does not exceed a specified maximum value.

16. The method according to claim 11, wherein the gas supply is controlled so that the gas pressure in the intermediate chambers (48, 50, 52) does not fall below a specified minimum value.

17. The method according to claim 15, wherein the gas pressure in the intermediate chambers (48, 50, 52) is regulated within an interval specified by the maximum value and the minimum value so that the gas pressure in the gas store chambers comes as close as possible to a target value.

18. The method according to claim 11, wherein an on-off control is performed.

19. The method according to claim 11, wherein the intermediate chambers (48, 50, 52) are each ventilated using at least one pressure regulating ventilation opening (49, 51, 53).

20. The method according to claim 11, wherein the regulation is controlled from a site remote from the biogas system.

* * * * *